United States Patent [19]

Galey et al.

[11] Patent Number: 5,536,500
[45] Date of Patent: Jul. 16, 1996

[54] MONOESTERS AND DIESTERS OF CINNAMIC ACID OR OF ONE OF THE DERIVATIVES THEREOF AND OF VITAMIN C, PROCESS FOR THE PREPARATION THEREOF, AND USE AS ANTIOXIDANTS IN COSMETIC, PHARMACEUTICAL OR NUTRITIONAL COMPOSITIONS

[75] Inventors: Jean-Baptiste Galey, Paris; Eric Terranova, Asnieres, both of France

[73] Assignee: L'Oreal, Paris, France

[21] Appl. No.: 376,218

[22] Filed: Jan. 20, 1995

[30]  Foreign Application Priority Data

Jan. 20, 1994 [FR] France ................................ 94 00583

[51] Int. Cl.$^6$ ............................. A61K 7/48; C07D 307/26
[52] U.S. Cl. ......................... 424/401; 514/474; 514/938; 549/315
[58] Field of Search ........................... 424/401; 514/474, 514/938; 549/315

[56]  References Cited

U.S. PATENT DOCUMENTS

| | | | |
|---|---|---|---|
| 3,318,914 | 5/1967 | Kobayashi et al. | 260/343.7 |
| 4,780,549 | 10/1988 | Terao et al. | 549/315 |
| 4,959,362 | 9/1990 | Terao et al. | 514/231.5 |

FOREIGN PATENT DOCUMENTS

| | | |
|---|---|---|
| 1000307 | 10/1988 | Belgium . |
| 0074411 | 3/1983 | European Pat. Off. . |
| 0146121 | 6/1985 | European Pat. Off. . |
| 0202589 | 11/1986 | European Pat. Off. . |
| 1196898 | 11/1959 | France . |
| 1374746 | 8/1964 | France . |
| 1530414 | 6/1968 | France . |
| 2580644 | 10/1986 | France . |

Primary Examiner—Jyothsna Venkat
Attorney, Agent, or Firm—Cushman Darby & Cushman

[57]  ABSTRACT

The present invention provides vitamin C derivatives and cosmetic, pharmaceutical and nutritional compositions containing same which impart protective properties against oxidation of lipidic constituents of the skin.

6 Claims, No Drawings

MONOESTERS AND DIESTERS OF CINNAMIC ACID OR OF ONE OF THE DERIVATIVES THEREOF AND OF VITAMIN C, PROCESS FOR THE PREPARATION THEREOF, AND USE AS ANTIOXIDANTS IN COSMETIC, PHARMACEUTICAL OR NUTRITIONAL COMPOSITIONS

The present invention concerns new monoesters and diesters of cinnamic acid or of one of the derivatives thereof and of vitamin C, a process for the preparation thereof, and their use as antioxidants in cosmetic or pharmaceutical compositions, not only for the purpose of protecting them against oxidation, but also for imparting to them protective properties against oxidation of the lipidic constituents of the skin.

As is well known, vitamin C, or ascorbic acid, is a naturally-occurring product found in many fruits and vegetables. This vitamin exhibits anti-scorbutic properties, since it contributes to the synthesis of collagen, the main constituent of the protein fibers in human tissue.

In fact, vitamin C allows hydroxylation of two amino acids, lysine and proline, by keeping the iron in the cofactor of the lysine and proline hydroxylases in the reduced state $Fe^{2+}$.

Vitamin C also plays a role in other oxidation and enzymatic hydroxylation processes, and, in particular, in the hydroxylation of the dopamine in noradrenaline catalyzed by dopamine β-hydroxylase, or in the hydroxylation of tryptophan in 5-hydroxytryptophan catalyzed by tryptophan hydroxylase.

In addition, vitamin C possesses reducing properties which gives it a natural anti-oxidizing function as described in the literature, particular in the journal of G. W. Burton and colleagues, *Adv. in Free Radical Biology and Medicine*, 419 (1986).

While, as just indicated, vitamin C possesses numerous indispensable biological properties, it nevertheless has some disadvantages, since it is self-oxidizable, heat-sensitive, and unstable "in vitro" in aqueous mediums, particularly in an alkaline pH.

To solve the problem of self-oxidation, several authors have considered stabilizing vitamin C using various methods. Among the latter, mention may be made of the formation of a chemical association of ascorbic acid and, for example, gluconic or urocanic acid.

Another method consists in stabilizing vitamin C using physical techniques, for example by incorporating in cyclodextrins zeolites or liposomes.

Furthermore, it has been suggested that vitamin C derivatives should be produced, in particular, as phosphodiesters in combination with vitamin E, for example.

A final stabilization method proposed would involve chemical functionalization of the enediol group of the vitamin C, by formation of a phosphate or sulfate function or of an ether or ester function.

In this respect, many authors have suggested monoesters in the second position in the vitamin C for the purpose of stabilizing it. These monoesters are mainly alkyl esters having from 1 to 18 atoms of carbon, fluoroalkyl esters having 2 to 7 atoms of carbon and from 4 to 15 atoms of fluorine, or alternatively, aryl esters and, in particular, potentially substituted benzoates.

It has now been found, surprisingly, that the esters of cinnamic acid or of one of the derivatives thereof and of vitamin C were much more stable under self-oxidation than were not only vitamin C, but also some of its derivatives already described in the literature. Moreover, it has been found, unexpectedly, that the compounds according to the invention were much more effective than vitamin C and its derivatives as regards the protection of epidermal cells subjected to the action of free radicals.

The main advantage of the monoesters and diesters of vitamin C according to the invention lies in the fact that the acyl group of these esters derives mainly from the structure of a naturally-occurring product, i.e., cinnamic acid, or of one of its derivatives such as ferulic, caffeic, or sinapic acid, which by themselves possess anti-oxidizing properties.

It has been shown, moreover, that the esters of vitamin C according to the invention have a much more pronounced lipophilic nature than does vitamin C, thereby allowing better penetration into the stratum corneum.

In addition, the esters of vitamin C according to the invention may be considered excellent carriers of vitamin C, since, in the presence of esterase-type epidermal enzymes, they can undergo hydrolysis, thus releasing vitamin C.

The present invention thus relates, under the heading of new compounds, to monoesters and diesters of cinnamic acid or one of its derivatives and of vitamin C, which correspond to the following general formula:

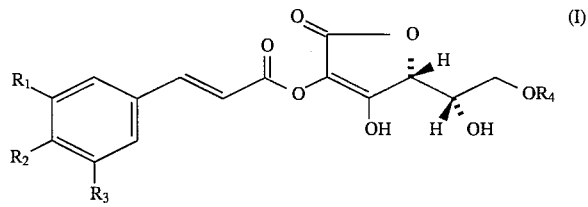

in which $R_1$, $R_2$ and $R_3$, whether identical or different, represent an atom of hydrogen, a hydroxy, alkoxy, fluoroalkoxy, or alkylcarbonyloxy radical; and $R_4$ represents an atom of hydrogen or —$COR_5$, $R_5$ being an alkyl radical at $C_1$–$C_{20}$ or the radical corresponding to the formula:

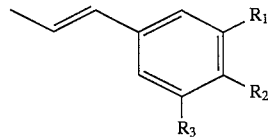

In accordance with the invention, the alkoxy radical is preferably a methoxy, ethoxy, or butoxy radical, the fluoroalkoxy radical is preferably a trifluoromethoxy radical, and the alkylcarbonyloxy radical is preferably an acetoxy, propionyloxy, or butyryloxy radical.

Among the compounds corresponding to formula (I) according to the invention, mention may be made, in particular, of:

2-O-ascorbyl cinnamate,

2-O-ascorbyl ferulate,

2-O-ascorbyl caffeate,

2-O-ascorbyl sinapate, and

2-O-[6-palmitoyl ascorbyl]-4'-acetoxy ferulate.

The compounds according to the invention may easily be synthesized in accordance with the following reaction diagram:

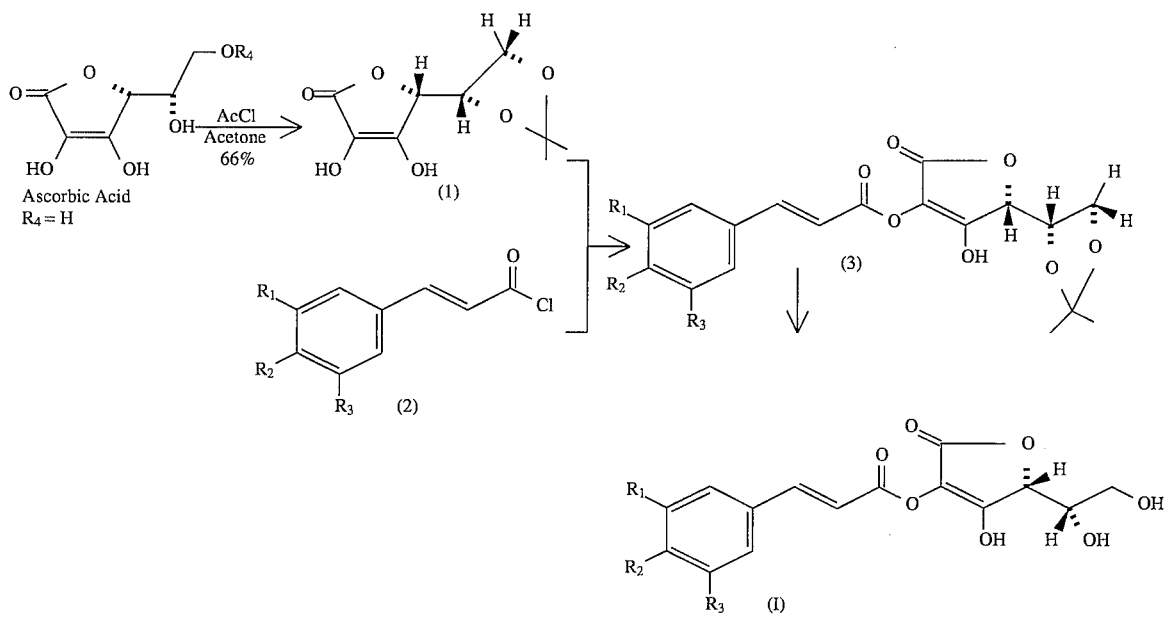

When $R_4$ represents an atom of hydrogen, the first step in the preparation of the monoesters consists in protecting the hydroxy functions in position 5 or 6 of the ascorbic acid, by forming a cyclical ketal of the 5,6-O-isopropylidene type obtained by reacting ascorbic acid in acetone in the presence of acetyl chloride used as catalyst. 5,6-O-isopropylidene ascorbic acid is obtained with a yield of about 65–70% and exists as a cottony white solid.

The acid chloride corresponding to formula (2) may be a commercial product, such as cinnamoyl chloride, or it can be produced by synthesis when it contains substituents on the aromatic ring, or it may be obtained from certain commercial acids, such as ferulic acid.

However, when one of the substituents $R_1$, $R_2$ or $R_3$ is a hydroxy group, it must be protected preliminarily, for example by acetylation of the corresponding hydroxylated aromatic acid in the presence of acetic anhydride or of a base such as 4-N,N-dimethylaminopyridine.

The acid chloride is then prepared by reacting acetylated aromatic acid with thionyl chloride in an organic solvent, such as toluene, at a temperature of between 50° and 120° C.

The acid chloride (2) and the 5,6-O-isopropylidene ascorbic acid (1) are reacted in an organic solvent, such as dichloromethane in the presence of imidazole, thereby producing the expected ester (3) in a yield of approximately 90%.

The group protecting the 5,6-dihydroxy functions of the ascorbic acid and, potentially, of the hydroxy function(s) of the aromatic ring is then removed by stirring the monoester obtained (3) in acetone in the presence of 1N to 3N HCl.

When, in formula (I), $R_4$ represents the —$COR_5$ radical, the compounds existing in diester form are first prepared by acylation in position 6 of the ascorbic acid using conventional methods; next, the ascorbyl ester obtained is reacted as indicated above with an acid chloride corresponding to formula (2).

Certain ascorbyl esters in position 6 are commercial products, such as 6-O-ascorbyl palmitate.

The effectiveness of the monoesters and diesters according to the invention has been studied in vitro by using keratinocytes from human epidermis in a first culture subjected to an oxidizing stress, such as the hypoxanthine-xanthine oxidase system, the action of UV light, or the addition of iron salts.

The oxidizing stress produces a disequilibrium of the antioxidant/pro-oxidant balance through formation of oxygenated free radicals, such as superoxide anions or the hydroxyl radicals. The activity of these free radicals leads to oxidative damage on the cellular constituents, in particular the cell membranes, thereby causing cell death.

The protective capacity of the compounds according to the invention has been studied in various concentrations by measuring the percentage of cells still living one hour after the oxidizing stress.

The results obtained revealed that the compounds according to the invention furnished an excellent protective activity at low concentrations, as compared with those of the compounds now used in cosmetic and pharmaceutical products, such as ascorbic acid and its principal derivatives described in the literature, such as 2-ascorbyl benzoate or 2-O-glucopyranosyl ascorbic acid. Thus, with respect to the hypoxanthine/xanthine oxidase system, keratinocytes are protected by micromolar concentrations of the compounds according to the invention, while, to achieve equivalent protection, over 1,000 times more free vitamin C would have to be used.

Although the mechanism of action has not been revealed with certainty, it is presumed to be indirect (reducing power) or direct (trapping of free radicals).

The present invention also relates to cosmetic, pharmaceutical or nutritional compositions containing fatty substances, characterized by the fact that they contain at least one monoester or diester of vitamin C corresponding to formula (I), previously specified as an anti-oxidant.

The fatty substances in the compositions according to the invention include, for example, animal fatty substances, e.g., monacetin (cetin), beeswax, lanolin, perhydrosqualene, turtle oil, etc.; vegetable fatty substances existing as oils, fats or waxes, e.g. sweet almond oil, avocado oil, olive oil, sesame oil, macadamia oil, hydrogenated copra or palm oil, cocoa butter, carnauba wax, montan wax; and synthetic oils composed of esters and/or ethers of glycerol or glycol, such as those described in FR-B 75.24656 (2,281,916), 75.24657 (2,281,743) and 75.24658 (2,281,744).

In addition to the relatively-oxidizable fatty substances, the cosmetic or pharmaceutical compositions may contain oxidation-sensitive products, such as vitamin F or β-carotene.

The compositions according to the invention may exist as an oleaginous solution, a water-in-oil or oil-in-water emulsion, a solid, possible anhydrous product, a lotion or microdispersion, a reticulate dispersion, ionic or nonionic vesicle-forming lipids, or a mixture of the foregoing products. They are also used in skin care lotions, creams (facial, hand, body, sunscreen, makeup removal or foundation creams), fluid foundations, makeup removal lotions, sunscreen lotions, bath oils, lipsticks, eyeliners, deodorant sticks, etc.

To allow topical application, the pharmaceutical compositions according to the invention contain vehicles and ingredients required to produce compositions in the form of an ointment, a cream, a lotion, or an oleaginous solution.

According to a preferred embodiment, the cosmetic or pharmaceutical skin compositions exist in a form intended to be applied topically, in particular as creams intended to provide protection against the oxidation of skin lipids.

In the compositions according to the invention, the monoesters and diesters of vitamin C corresponding to general formula (I) as specified above are normally present in proportions of from 0.01 and 5% by weight of the total weight of the composition.

Moreover, the compositions according to the invention may contain active compounds or ingredients used conventionally in the compositions mentioned above, such as surfactants, dyes, perfumes, astringents, ultraviolet-absorbing products, and organic solvents. These compositions are prepared using customary methods.

As illustrations several examples of the preparation of monoesters or diesters of cinnamic acid or one of its derivatives and of vitamin C corresponding to the general formula (I), are hereinafter given as well as examples of cosmetic and pharmaceutical compositions containing the same.

EXAMPLES OF PREPARATION

Example 1: Preparation of 2-O-ascorbyl ferulate (1) Preparation of 4-acetoxy ferulic acid In a 250 ml three-necked bottle equipped with a cooling apparatus, a thermometer and a magnetic stirring apparatus, 16.4 grams ferulic acid (0.084 mole) were added to 50 ml of acetic anhydride and 0.51 g 4-N,N-dimethylaminopyridine. After stirring the reactive medium at ambient temperature for 3 hours and 45 minutes, the medium was hydrolyzed with 100 ml of water.

After stirring overnight, the product was filtered, rinsed in water (2×100 ml), and vacuum-dried on $P_2O_5$ at ambient temperature. 20 g 4-acetoxy ferulic acid (0.084 mole) was collected (yield—100%) in the form of a white powder.

Melting point—199°–200° C. (Köfler)

Rf (Silica gel: MERCK 60 F254®)=0.41 ($CH_2Cl_2$:$CH_3OH$=9:1).

RMN $^1$H (DMSO d6; 200 MHz) 2.09 (S; $CH_3CO$); 3.65 (S; $CH_3O$); 6.43 (d; C=CH–CO; J=16 Hz); 6.94 (d; Ar-H; $J_1$=8.2 Hz); 7.09 (dxd; Ar-H; $J_1$=8.2 Hz and $J_2$=1.4 Hz); 7.30 (d; Ar-H; $J_2$=1.4 Hz); 7.74 (d; Ar-CH=C; J=16 Hz); 12.24 (large S; CO—OH)

RMN $^{13}$C (DMSO d6; 50 MHz) 20.3; 55.9; 111.8; 119.5; 121.3; 123.2; 133.3; 140.8; 143.3; 151.2; 167.6; 168.4

Ultimate analysis: $C_{12}H_{12}O_5$; Molecular weight=236

|  | % C | % H | % O |
|---|---|---|---|
| Calculated | 61.02 | 5.09 | 33.90 |
| Actually found | 59.92 | 5.08 | 33.94 |

(2) Preparation of 4-acetoxy ferulic acid chloride

In a 500 ml three-necked bottle equipped with a thermometer, an argon feed, a cooling apparatus covered by a calcium chloride guard, and a magnetic stirring apparatus, 12.2 g 4-acetoxy ferulic acid (0.051 mole) as obtained above and 15 ml thionyl chloride (d=1.64; 0.204 mole) were added to 200 ml toluene. The medium was heated under argon for one hour under solvent reflux; the toluene was then drained away using a rotary evaporator. The raw product obtained was either used directly in the step involving coupling with 5,6-O-isopropylidene ascorbic acid, or recrystallized in 50 ml toluene. After vacuum-drying for 24 hours on $P_2O_5$ at ambient temperature, 9.32 grams 4-acetoxy ferulic acid chloride (0.037 mole) were collected; yield=72% in the form of pale yellow crystals.

Melting point=139°–140° C. (Köfler)

RMN $^1$H (CDCl$_3$; 200 MHz) 2.24 (S; AcO); 3.76 (S; $CH_3O$); 6.49 (d; C=CH–CO; J=15.5 Hz); 6.98–7.10 (m; 3×Ar-H); 7.68 (d; Ar-CH=C; J=15.5 Hz);

RMN $^{13}$C (CDCL$_3$; 50 MHz) 21.5; 56.8; 112.8; 123.2; 123.4; 124.5 132.7; 143.7; 150.8; 152.5; 166.8; 169.4

Ultimate analysis: $C_{12}H_{11}ClO_5$; Molecular weight=254

|  | % C | % H | % Cl | % O |
|---|---|---|---|---|
| Calculated | 56.60 | 4.35 | 13.92 | 25.13 |
| Actually found | 56.86 | 4.43 | 13.87 | 25.64 |

(3) Preparation of 5,6-O-isopropylidene ascorbic acid 100 g L-ascorbic acid (0,568 mole) and 1.1 liter acetone were added to a 2-liter three-necked bottle equipped with a mechanical stirring apparatus, a cooling apparatus, and a thermometer. 2 ml acetyl chloride (0.028 mole) were added, and the medium was heated to 40° C. After 3 hours 30 minutes reaction time, the reactive medium was cooled to 15° C., then filtered. The solid was taken up while stirring in 400 ml ethyl acetate and filtered again. After vacuum-drying on $P_2O_5$ for 24 hours, 80.8 g 5,6-O-isopropylidene ascorbic acid (0.374 mole) were collected;

yield=65.8% in the form of a cottony white solid.

Melting point=202°–203° C. (Köfler)

Rf (Silica gel: MERCK 60 F254®)=0.6 ($CH_2Cl_2$: $CH_3OH$=3:1).

RMN $^1$H (DMSO d6; 200 MHz) 1.29 (S; 2×$CH_3$; 3.88–3.95 (m; $C_6$–H); 4.07–4.17 (m; $C_6$–H; 4.26–4.34 (m; $c_5$–H); 4.72–4.75 (m; $c_4$–H); 8.49 (large S; $C_3$–OH); 11.28 (large S; $C_2$–$OH_).$ RMN $^{13}$C (DMSO d6; 50 MHz) 25.4; 25.8; 64.9; 73.5; 74.2; 109; 118.2; 152.3; 170.2

Ultimate analysis: $C_9H_{12}O_6$; Molecular weight=216

|  | % C | % H | % O |
|---|---|---|---|
| Calculated | 50.00 | 5.56 | 44.44 |
| Actually found | 49.88 | 5.59 | 44.27 |

(4) Preparation of 2-O-[5,6-O-isopropylideneascorbyl]-4'-acetoxy ferulate

In a 500 ml three-necked bottle equipped with a cooling apparatus, a thermometer, an adding funnel, and a magnetic stirring mechanism, 7.70 g (113 mmoles) imidazole were added to 150 ml dichloromethane. 14.4 g (57 mmoles) 4-acetoxy ferulic acid chloride in solution in 120 ml dichloromethane were then dripped in at ambient temperature (20° ).

After stirring for one hour, 12.2 g (57 mmoles) 5,6-O-isopropylidene ascorbic acid and 60 ml dichloromethane were added. The mixture was stirred for three hours at ambient temperature. The dichloromethane was evaporated, and the raw product was taken up in 100 ml tert-butanol until it was dissolved. 60 ml 1n HCl (60 mmoles) and 300 ml water were then added. After stirring for 30 minutes, the precipitate obtained was filtered, washed in water, and vacuum-dried on $P_2O_5$. 22.7 g 2-O-[5,6-O-isopropylidene-ascorbyl]-4'-acetoxy ferulate (52 mmoles) were obtained; yield=92%.

After recrystallization in isopropyl alcohol, 15.3 g of the expected purfied product were obtained (yield=62%).

Melting point=197°–198° C. (Köfler)

Rf (Silica gel: MERCK 60 F254®)=0.63 ($CH_2Cl_2$: $CH_3OH$: 20% $NH_4OH$=78:20:2)

RMN $^1$H (DMSO d6; 500 MHz) 1.28 (S; 2×$CH_3$); 2.28(S; AcO); 3.84 (S; $OCH_3$); 3.96 (dxd; $C_6$-H); $J_1$=8.5 HZ and $J_2$=6 Hz); 4.15 (dxd; $C_6$-H; $J_1$=8.5 Hz and $J_3$=7 Hz); 4.41 (dxdxd; $C_5$-H; $J_2$=6 Hz; $J_3$=7 Hz; $J_4$=2.5 Hz); 5.03 (d; $C_4$-H; $J_4$=2.5 Hz); 6.88 (d; C=CH–CO; $J_5$=16 Hz); 7.17 (d; Ar–H; $J_6$=8.5 HZ); 7.40 (dxd; Ar–H; $J_6$=8.5 Hz; $J_7$=2 Hz ); 7.60 (d; Ar–H; $J_7$=2 Hz); 7.82 (d; Ar–CH=C; $J_5$–16 Hz); 12.94 (large S; $C_3$–OH);

RMN $^{13}$C (DMSO d6; 50 MHz) 20.5; 25.4; 25.8; 56.1; 73.3; 75.2; 109.3; 112,3; 112.5; 116.6; 121.9; 123.4; 132.9; 141.5; 146.4; 151.3; 163.4; 163.5; 167.9; 168.5

Ultimate analysis: $C_{21}H_{22}O_{10}$; Molecular weight=434

|  | % C | % H | % O |
| --- | --- | --- | --- |
| Calculated | 58.08 | 5.10 | 36.83 |
| Actually found | 58.13 | 5.26 | 36.60 |

(5) Preparation of 2-O-ascorbyl ferulate

In a 250 ml three-necked bottle equipped with a thermometer, a cooling apparatus, and a magnetic stirring mechanism, 6.7 g 2O-[5,6-O-isopropylideneascorbyl]-4'-acetoxy ferulate (15.4 mmoles) were incorporated into 70 ml acetone; 48 ml 1N HCl (48 mmoles) were then added. The medium was stirred for 48 hours at ambient temperature; the acetone was then evaporated using a rotary evaporator. The aqueous phase was then extracted using 4×50 ml ethyl acetate, and the organic phases collected were dried on sodium sulfate. After concentration to a volume of approximately 15 ml ethyl acetate, the medium was cooled and the precipitate filtered. 1.95 g 2-O-ascorbyl ferulate (5.5 mmoles) were collected. Yield=36%.

Melting point=157°–158° C. (Köfler)

Rf (Silica gel: Merck 60 F254)=0.14 ($CH_2C_{12}/CH_{30}H/NH_4OH$ (20%) 78/20/2)

RMN $^1$H (DMSO d6; 500 MHz) 3.48 (m; 2×$C_6$–H); 3.80 (m; $C_5$–H+$OCH_3$); 4.94 (d; $C_4$–H; $J_1$=1.5 Hz); 5.07 (large S; $C_5$–OH and $C_6$–OH); 6.61 (d; C=CH–CO; $J_2$=16 Hz); 6.81 (d; Ar–H; $J_3$=8.5 Hz); 7.20 (dxd; ArH; $J_3$=8.5 Hz and $J_4$=2 Hz); 7.40 (d; Ar–H; $J_4$=2 Hz); 9.70 (S; Ar–OH); 12.56 (large S; $C_3$–OH) .

RMN $^{13}$C (DMSO d6; 125 MHz) 55.73 ($c_{16}$); 61.73 ($C_6$); 68.60 ($C_5$); 75.43 ($C_4$); 111.60 ($C_{11}$); 112.34 ($C_2$); 112.58 ($C_8$); 115.56 ($C_{14}$); 123.59 ($C_{15}$) 125.35 ($C_{10}$); 147.32 ($C_9$); 147.96 ($C_2$); 149.85 ($C_{13}$); 163.70 ($C_3$); 163.73 ($C_7$); 168.12 ($C_1$).

The position of the ester function on the vitamin C was determined by two-dimensional proton-carbon RMN in the DMSO d6.

Ultimate analysis: $C_{16}H_{16}O_9$; Molecular weight=352

|  | % C | % H | % O |
| --- | --- | --- | --- |
| Calculated | 54.55 | 4.58 | 40.87 |
| Actually found | 54.21 | 4.62 | 40.72 |

Example 2: Preparation of 2-O-ascorbyl cinnamate (1) Preparation of 2-O-[5,6-O-isopropylideneascorbyl] cinnamate 2.70 g (0.04 mole) imidazole were dissolved in a suitable flask in 20 ml chloroform; then, 3.3 g (0.02 mole) of the cinnamic acid chloride in solution in 40 ml chloroform were dripped in while keeping the temperature at approximately 20° C. using a cold water bath.

After stirring for one hour at ambient temperature, 4.30 g (0.02 mole) 5,6-O-isopropylidene ascorbic acid (such as that obtained in Example 1(3)) were added in solution in 50 ml chloroform.

After stirring for two hours at ambient temperature, the reactive medium was extracted using 100 ml of a 5% sodium bicarbonate solution. The aqueous phase was acidified to a pH of 1 using dilute HCl and extracted twice with 50 ml dichloromethane.

After decanting and drying on $Na_2SO_4$ and evaporation, 5.20 g 2-O-[5,6-O-isopropylideneascorbyl] cinnamate were obtained; yield=75%.

After recrystallization of the precipitate in 25 ml ethyl acetate, 4.05 g of the expected ester were obtained; yield= 58%.

Melting point=166°–168 ° C. (Köfler)

RMN $^1$H (CDCl$_3$; 500 MHz) 1.40 (S; $CH_3$); 1.42 (S; $CH_3$); 4.12(dxd; $C_6$–H); 4.22 (dxd; $C_6$–H; 4.45 (dxd; $C_5$–H); 4.72 (d; $C_4$–H); 6.63 (d; C=CH–CO); 7.45 (m; 3×Ar–H); 7.58 (d; 2×Ar–H); 7.93 (d; Ar–CH=C); 10.29 (S; C=$C_3$–OH );

RMN$^{13}$C (CDCl$_3$; 125 MHz) 25.32; 25.51; 65.07; 73.27; 74.38; 110.42; 114.08; 115.28; 128.55; 128.92; 131.52; 133.07; 150.14; 154.67; 166.05; 166.43

Ultimate analysis: $C_{18}H_{18}O_7$; Molecular weight=352

|  | % C | % H | % O |
| --- | --- | --- | --- |
| Calculated | 62.43 | 5.20 | 32.37 |
| Actually found | 62.24 | 5.17 | 32.19 |

(2) Preparation of 2-O-ascorbyl cinnamate

In a 250 ml three-necked bottle, 4.85 g (0.014 mole) 2-O[5,6-O-isopropylideneascorbyl] cinnamate were incorporated into 100 ml methanol; 14 ml 1N HCl were then added.

After stirring for 24 hours at ambient temperature, the reactive medium is dry-evaporated, taken up in 50 ml water, then extracted three times using 50 ml ethyl acetate. After drying the organic phase on $Na_2SO_4$ and evaporation, the resulting precipitate was taken up in 55 ml of a 90/10 isopropyl ether/acetone mixture and stirred for four hours.

After filtration on sintered glass, 2.80 g 2-O-ascorbyl cinnamate were obtained. Yield=66%.

Melting point=144°–146° C. (Köfler)

RMN $^1$H (CDCl$_3$; 500 MHz) 3.47 (m; 2×C$_6$–H); 3.81 (m; C$_5$H); 4.96 (d; C$_4$–H); 5.1 (S; C$_5$–OH+C$_6$OH); 6.80 (d: C=CH–CO); 7.46 (m; 3×Ar–H); 7.80(m; 2×Ar–H+Ar–CH=C); 12.62 (S; =C$_3$-OH;

RMN $^{13}$C (CDCl$_3$; 125 MHz) 61.73; 68.82; 75.49; 112.19; 116.29; 128.65; 128.99; 130.94; 133.75; 146.76; 163.36; 163.91; 168.00

Ultimate analysis: C$_{15}$H$_{14}$O$_7$; Molecular weight=306

|  | % C | % H | % O |
|---|---|---|---|
| Calculated | 58.82 | 4.57 | 36.60 |
| Actually found | 58.74 | 4.69 | 36.61 |

Example 3: Preparation of 2-O-[6-palmitoyl ascorbyl]-4'-acetoxy ferulate

In a 250 ml three-necked bottle, 2.95 g imidazole were added to 130 ml dichloromethane. Next, 5.5 g 4-acetoxy ferulic acid chloride (obtained in Example 1(2)) in solution in 50 ml dichloromethane were dripped in at ambient temperature.

After stirring for one hour, 8.95 g 6-palmitate ascorbyl were added, and the mixture was stirred for three hours at ambient temperature. The dichloromethane was evaporated, and the raw product was taken up in 30 ml tert-butanol until an oil was obtained. At that stage, 25 ml 1N acid chloride, then 100 ml water were added. After stirring for 30 minutes, the resulting precipitate was filtered, washed in water, and vacuum-dried on P$_2$O$_5$. 13.75 g 2-O-[6-palmitoyl ascorbyl]-4'-acetoxy ferulate were collected.

Characterization: $^{13}$C 2D proton spectra consistent with the structure.

RMN $^1$H (CDCl$_3$): δ (ppm) 0.873 (t, 3H); 1.26 (m, 26H); 1.62 (m, 2H); 2.32(s, 3H); 2.37 (t, 2H); 3.88 (s, 3H); 4.28 (m, 2H); 4.41 (dd, 1H); 4.86 (d, 1H); 6.58 (d, 1H); 7.09 (d, 1H); 7.15 (d, 1H);

RMN $^{13}$C (CDCl$_3$): δ (ppm) 14.12; 20.64; 22.7; 24.86; 29.5; 31.93; 34.1; 56.03; 64.65; 68.13; 75.5; 111.59; 114.4; 115.46; 122.41; 123.6; 132.2; 142.76; 149.65; 151.7; 155.4; 166.47; 168.6; 173.98.

COMPOSITION EXAMPLES

Example A

An oil-in-water emulsion was prepared by mixing the following ingredients:

| | |
|---|---|
| 2-O-ascorbyl cinnamate | 0.1% |
| Polyethylene glycol oxyethylenated with 50 moles OE | 3% |
| Diglycerol monostearate | 3% |
| Vaseline oil | 24% |
| Cetyl alcohol | 5% |
| Water, sufficient amount for | 100% |

Example B

An oil-in-water emulsion was prepared by mixing the following ingredients:

| | |
|---|---|
| 2-O-ascorbyl ferulate | 0.1% |
| Octyl palmitate | 10% |
| Glycerol mono-isostearate | 4% |
| Vaseline oil | 24% |
| Vitamin E | 1% |
| Glycerol | 3% |
| Water, sufficient amount for | 100% |

Example C

The following composition was prepared as a cream by mixing the following ingredients:

| | |
|---|---|
| 2-O-ascorbyl ferulate | 0.1% |
| Jojoba oil | 13% |
| Methyl/propylparaben mixture | 0.05% |
| Potassium sorbate | 0.3% |
| Cyclopentadimethylsiloxane | 10% |
| Stearyl alcohol | 1% |
| Stearic acid | 4% |
| Polyethylene glycol stearate | 3% |
| Glycerol | 3% |
| Water, sufficient amount for | 100% |

In this example, 2-O-ascorbyl ferulate can be replaced by an identical quantity of 2-O-[6-palmitoyl ascorbyl]-4'-acetoxy ferulate.

The compositions in Examples A to C are particularly stable over time. Moreover, they provide effective protection of the epidermal cells exposed to free radical activity.

We claim:

1. Vitamin C derivatives corresponding to the following formula:

(I)

wherein

R$_1$, R$_2$ and R$_3$, identical or different, represent a hydrogen atom, a hydroxy, an alkoxy radical selected from the group consisting of methoxy, ethoxy, and butoxy, a trifluoromethoxy radical, or an alkylcarbonyloxy radical selected from the group consisting of acetoxy, propionyloxy, and butyryloxy, and R$_4$ represents a hydrogen atom or —COR$_5$, R$_5$ representing a C$_1$–C$_{20}$ alkyl radical or the radical corresponding to the formula:

2. The vitamin C derivatives according to claim 1 which are selected from the group consisting of:

2-O-ascorbyl cinnamate,

2-O-ascorbyl ferulate,

2-O-ascorbyl caffeate,

2-O-ascorbyl sinapate, and

2-O-[6-palmitoyl ascorbyl]-4'-acetoxy ferulate.

3. A cosmetic, pharmaceutical or nutritional composition, containing in a suitable cosmetic, pharmaceutical or nutritional vehicle, at least one oxidizable fatty substance and at least one vitamin C derivative of formula (I) according to claim 1.

4. The composition according to claim 3, wherein said at least one vitamin C derivative of formula (I) is selected from the group consisting of:

2-O-ascorbyl cinnamate,

2-O-ascorbyl ferulate,

2-O-ascorbyl caffeate,

2-O-ascorbyl sinapate, and

2-O-[6-palmitoyl ascorbyl]-4'-acetoxy ferulate.

5. The composition according to claim 3 which contains from 0.01 to 5% by weight based on the total weight of the composition of the at least one vitamin C derivative of formula (I).

6. A cosmetic composition for protecting skin from lipid oxidation containing in a suitable vehicle for a topical application from 0.1 to 5% by weight based on the total weight of the composition of at least one vitamin C derivative of formula (I) according to claim 1.

* * * * *